US00PP20635P2

(12) United States Plant Patent
Meilland

(10) Patent No.: US PP20,635 P2
(45) Date of Patent: Jan. 5, 2010

(54) SHRUB ROSE PLANT NAMED 'MEISENTMIL'

(50) Latin Name: *Rosa bybrida*
Varietal Denomination: Meisentmil

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/285,420

(22) Filed: Oct. 3, 2008

(51) Int. Cl.
*A01H 5/00* (2006.01)

(52) U.S. Cl. ..... Plt./104

(58) Field of Classification Search ..... Plt./104
See application file for complete search history.

*Primary Examiner*—Kent L Bell
(74) *Attorney, Agent, or Firm*—Buchanan Ingersoll & Rooney PC

(57) ABSTRACT

A new and distinct variety of Shrub rose plant is provided that forms in abundance on a substantially continuous basis attractive slightly fragrant semi-double blossoms that are yellow to cream-yellow in coloration. The buds are globular in shape. The vegetation is vigorous and a spreading growth habit is displayed. The disease resistance is above average for the class with respect to Black Spot, Powdery Mildew, and Rust. The plant is particularly well suited for providing attractive ornamentation in the landscape, and can be grown as a ground cover.

1 Drawing Sheet

Figure 1:
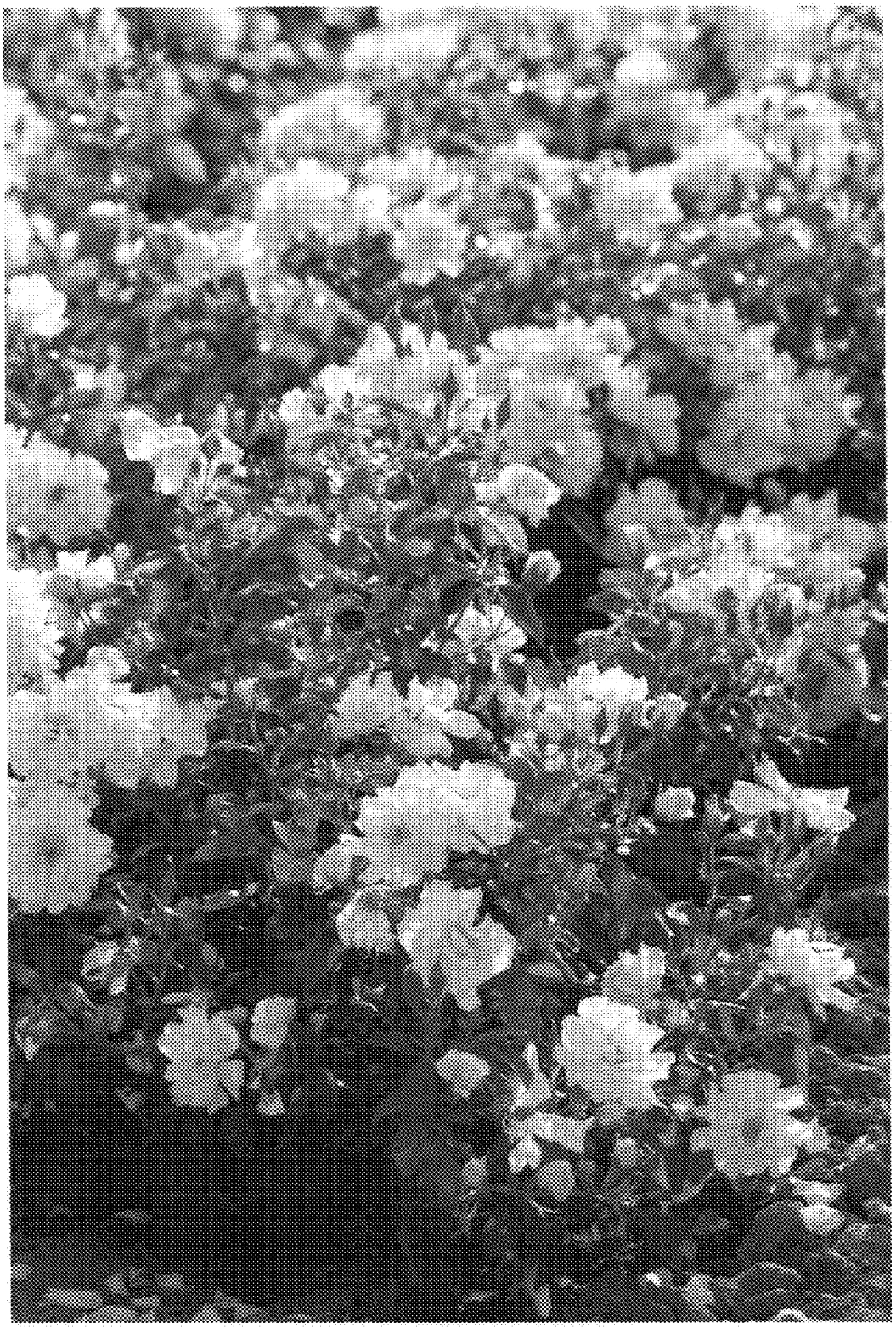

Botanical/commercial classification: *Rosa hybrida*/Shrub Rose Plant.

Varietal denomination: cv. Meisentmil.

SUMMARY OF THE INVENTION

The new variety of *Rosa hybrida* Shrub rose plant was created during May 1998 in France by artificial pollination wherein two parents were crossed which previously had been studied in the hope that they would contribute the desired characteristics. The female parent (i.e., the seed parent) was the 'Meiranovi' variety (U.S. Plant Pat. No. 6,385). The male parent (i.e., the pollen parent) was the product of the cross of the 'Korimro' variety (non-patented in the United States) and the 'Meibaltaz' variety (U.S. Plant Pat. No. 8,449). The 'Meiranovi' variety is marketed under the ANTHONY MEILLAND trademark, and the 'Korimro' variety is marketed under the IMMENSEE trademark.

The parentage of the new variety can be summarized as follows:

'Meiranovi'×('Korimro'×'Meibaltaz')

The seeds resulting from the above pollination were sown and small plants were obtained which were physically and biologically different from each other. Selective study resulted in the identification during June 2001 of a single plant of the new variety.

It was found that the new Shrub rose plant of the present invention:

(a) displays a vigorous spreading growth habit,
(b) forms on a substantially continuous basis attractive small semi-double blossoms that are yellow to cream-yellow in coloration,
(c) displays attractive light green foliage having a matte finish,
(d) displays above average disease resistance for the class, and
(e) is particularly well suited for providing attractive ornamentation.

The new variety well meets the needs of the horticultural industry and can be grown to advantage in parks and gardens. It is particularly well suited for growing in small areas where an attractive ground cover is desired.

The new variety can be readily distinguished from its ancestors. For instance, the blossoms are different than those of the 'Meiranovi', 'Korimro', and 'Meibaltaz' varieties. More specifically, the 'Meiranovi' variety forms pink blossoms, the 'Korimro' variety forms pink to near white blossoms, and the 'Meibaltaz' variety forms double blossoms having more petals and an aureolin yellow coloration.

The new variety of the present invention also can be readily distinguished from the 'Meidrifora' variety (U.S. Plant Pat. No. 19,148), and the 'Meijocos' variety (U.S. Plant Pat. No. 18,874). The 'Meidrifora' variety forms deep coral-orange blossoms, and the 'Meijocos' variety forms deep pink blossoms.

The new variety has been found to undergo asexual propagation at Wasco, Calif., U.S.A., by a number of routes, including budding, grafting, and the use of cuttings. Such asexual propagation by the above-mentioned techniques has shown that the characteristics of the new variety are stable and are strictly transmissible by such asexual propagation from one generation to another. Accordingly, the new variety undergoes asexual propagation in a true-to-type manner.

The new variety has been named 'Meisentmil', and is being marketed under the LEMON SPLASH trademark.

BRIEF DESCRIPTION OF THE PHOTOGRAPH

The accompanying photograph of FIG. 1 shows as nearly true as it is reasonably possible to make the same, in a color illustration of this character, typical specimens of the new variety. Floral buds and blossoms in various stages of development are shown as well as the attractive light green foliage.

The illustrated plants were approximately two years of age and were being grown outdoors at Wasco, Calif., U.S.A.

DETAILED DESCRIPTION

The chart used in the identification of the colors is that of The Royal Horticultural Society (R.H.S. Colour Chart) except where ordinary color terms are utilized. Such common color terms are to be accorded their customary dictionary significance. The description is based upon the observation of a plant of the new variety at an age of approximately four years during the month of July while being grown outdoors near West Grove, Pa., U.S.A.

Class: Landscape Shrub Rose.

Plant:

*Growth habit.*—Vigorous and spreading.

*Blooming habit.*—Substantially continuous.

*Height.*—Commonly approximately 1.5 m at an age of four years.

*Width.*—Commonly approximately 0.75 m at an age of four years.

Branches:

*Length.*—Commonly approximately 30 to 40 cm on average for a four-year-old plant at the end of the season.

*Diameter.*—Commonly approximately 8 mm on average for a four-year-old plant at the end of the season.

*Color.*—Young stems: commonly near Yellow-Green Group 144B. Adult wood: commonly near Yellow-Green Group 147B.

*Thorns.*—Size: commonly approximately 0.7 cm in length, and approximately 0.7 cm in width at the base. Color: commonly near Brown Group 200D.

Leaves:

*Size.*—Length: approximately 5 cm on average for a leaf consisting of 5 leaflets. Width: approximately 3.5 cm on average for a leaf consisting of 5 leaflets.

*Leaflets.*—Shape: generally oblanceolate. Number: commonly 5 (most common) or 7. Length: a terminal leaflet commonly measures approximately 3 cm on average. Width: a terminal leaflet commonly measures approximately 1.5 cm on average. Apex shape: acute. Base shape: cuneate. Serration: small and single. Texture: generally very smooth with a protruding central vein, and a matte finish. Color: near Yellow-Green Group 146A on the upper surface, and near Yellow-Green Group 146C on the under surface.

Inflorescence:

*Bearing.*—Commonly in clusters.

*Peduncle.*—Commonly approximately 2.5 cm in length on average, approximately 2 mm in diameter on average, and near Yellow-Green Group 145A in coloration.

*Sepals.*—Number: 5. Shape: elongated commonly with an acuminate to aristate apex and smooth margins. Length: commonly approximately 1.5 cm on average. Width: commonly approximately 0.5 cm on average. Texture: tomentose on the upper surface and smooth on the under surface. Color: near Yellow-Green Group 147D on the upper surface, and near Yellow-Green Group 144A on the under surface.

*Buds.*—Shape: globular. Length: approximately 1.5 cm on average. Width: approximately 1 cm at the widest point on average. Color as calyx breaks: commonly near Yellow-Orange Group 14B.

*Flower.*—Shape: semi-double and informal. Diameter: approximately 3.5 cm on average. Depth: commonly approximately 1 cm on average. Color (newly opened): upper surface: Yellow Group 6A. under surface: Yellow Group 7B. Color (when mature): upper surface: Yellow Group 8C. under surface: Yellow Group 8C. Color (at end of blooming): upper surface: Yellow Group 10C. under surface: Yellow Group 11B. Color stability: color lightens with the progress of full maturity. Fragrance: slight and sweet. Petal number: approximately 16 on average under normal growing conditions. Petal arrangement: imbricated and spiraled. Petal shape: generally ovate. Petal length: commonly approximately 2.1 cm on average. Petal width: commonly approximately 1.2 cm on average. Petal apex: generally cuspidate. Petal base: generally cuneate. Petal margins: smooth. Lastingness: blossoms commonly last approximately 5 days on average when cut and placed in a vase. Petal drop: good with the petals commonly detaching cleanly before drying. Stamen number: approximately 35 on average. Anthers: regularly arranged around the styles, and near Yellow-Orange Group 17A in coloration. Filaments: near Yellow-Orange Group 17B in coloration. Pistils: approximately 18 on average. Styles: commonly near Greyed-Yellow Group 162B in coloration. Hips: commonly observed beginning in mid-August at a medium frequency, substantially round and approximately 1.5 cm in diameter, smooth in texture, and Yellow-Green Group 144A in coloration.

Development:

*Vegetation.*—Vigorous.

*Blooming.*—Abundant and substantially continuous.

*Tolerance to diseases.*—Above average for the class with respect to Black Spot, Mildew, and Rust.

I claim:

1. A new and distinct Shrub rose plant characterized by the following characteristics:

(a) displays a vigorous spreading growth habit, (b) forms on a substantially continuous basis attractive small semi-double blossoms that are yellow to cream-yellow in coloration, (c) displays attractive light green foliage having a matte finish, (d) displays above average disease resistance for the class, and, (e) is particularly well suited for providing attractive ornamentation;

substantially as shown and described.

* * * * *